United States Patent [19]

Campbell

[11] Patent Number: 4,988,660
[45] Date of Patent: Jan. 29, 1991

[54] DOUBLE PEROVSKITE CATALYSTS FOR OXIDATIVE COUPLING

[75] Inventor: Kenneth D. Campbell, Charleston, W. Va.

[73] Assignee: Union Carbide Chemicals and Plastics Company Inc., Danbury, Conn.

[21] Appl. No.: 542,699

[22] Filed: Jun. 25, 1990

[51] Int. Cl.$^5$ .................... B01J 23/10; B01J 23/78; B01J 23/84
[52] U.S. Cl. .................. 502/303; 502/302; 502/304; 502/525
[58] Field of Search ............... 502/302, 303, 304, 330, 502/525

[56] References Cited

U.S. PATENT DOCUMENTS

| 4,172,810 | 10/1919 | Mitchell, III et al. | 502/302 |
| 4,205,194 | 5/1980 | Mitchell, III et al. | 585/407 |
| 4,239,658 | 11/1980 | Mitchell, III et al. | 252/465 |

OTHER PUBLICATIONS

Keller, G. E., et al., "Synthesis of Ethylene Via Oxidative Coupling of Methane", J. Cataly., vol. 73, pp. 9-19 (1982).

Garcia, et al., "Direct Catalytic Synthesis of Ethylene from Methane", React. Kinet. Catal. Lett., vol. 28, 481 (1985).

Sofranko, J., et al., "The Oxidative Conversion of Methane to Higher Hydrocarbons", J. Cataly., vol. 103, pp. 302-310 (1987).

Jones, C. A., et al., "The Oxidative Conversion of Methane to Higher Hydrocarbons Over Alkali-Promoted Mn/SiO$_2$", J. Cataly., vol. 103, 311 (1987).

Gaffney A., et al., "Oxidative Coupling of Methane over Sodium Promoted Praseodymium Oxide", J. Cataly., vol. 114, pp. 422-432 (1988).

Vallet-Regi, M., et al., "Synthesis and Characterization of a New Double Perovskite: LaCaMnCoO$_6$", J. Chem. Soc., Dalton Trans., 775 (1988).

*Primary Examiner*—W. J. Shine
*Attorney, Agent, or Firm*—Jean B. Mauro

[57] ABSTRACT

Alkali metal doped double perovskites containing manganese and at least one of cobalt, iron and nickel are useful in the oxidative coupling of alkane to higher hydrocarbons.

5 Claims, No Drawings

DOUBLE PEROVSKITE CATALYSTS FOR OXIDATIVE COUPLING

This application is a division of Ser. No. 463,320 filed on Jan. 10, 1990.

This invention was made under United States of America Government support under Contract No. DE-AC22-87PC79817 awarded by the Department of Energy. The Government has certain rights in this invention.

This invention relates to processes using catalysts having enhanced initial $C_2$ selectivity for the oxidative coupling of lower molecular weight alkane to higher molecular weight hydrocarbons.

BACKGROUND OF THE INVENTION

Processes for the conversion of lower molecular weight alkanes such as methane to higher molecular weight hydrocarbons which have greater value are sought. One of the proposals for the conversion of lower molecular weight alkanes is by oxidative coupling. For instance, G. E. Keller and M. M. Bhasin disclose in Journal of Catalysts. Volume 73, pages 9 to 19 (1982) that methane can be converted to, e.g., ethylene. The publication by Keller, et al., has preceded the advent of substantial patent and open literature disclosures by numerous researchers pertaining to processes for the oxidative coupling of lower alkanes and catalysts for such Processes.

In order for an oxidative coupling process to be commercially attractive, the process should be capable of providing a good rate of conversion of the lower alkanes with high selectivity to the sought higher molecular weight hydrocarbons. Since conversion and selectivity can be enhanced by catalysts, catalytic processes have been the thrust of work done by researchers in oxidative coupling.

Two general types of oxidative coupling processes are the sequential, or pulsed, processes and the cofeed processes. In the cofeed processes, an oxygen-containing gas and an alkane-containing gas are simultaneously fed to a reaction zone. The sequential processes are characterized by alternately cycling an oxygen-containing gas and an alkane-containing gas to a reaction zone containing the catalyst. The sequential processes have an advantage in that the reactant and hydrocarbon products are not in contact with gas phase oxygen and this results in a minimization of the undesired and unselective homogeneous oxidation of the reactant or hydrocarbon products and in the ability to avoid potentially explosive mixtures of hydrocarbon and oxygen. Also, air can be used as the source for the oxygen-containing gas.

Group VIII metals have been proposed as components in oxidative coupling catalysts, but their potential has been severely limited. Keller, et al., supra, evaluated numerous metal components for oxidative coupling in a pulsed mode system. They concluded in FIG. 6 that iron, nickel, copper, silver and platinum have, in the pulsed system, no activity above that of bare support and that cobalt possibly has a small activity above that of bare support.

Mitchell, et al., in U.S. Pat. Nos. 4,172,810; 4,205,194 and 4,239,658 propose multicomponent catalysts containing a Group VIII noble metal having a molecular weight of 45 or greater, nickel or a GrouP IB noble metal having an atomic number of 47 or greater; a Group VIB metal oxide and a Group IIA metal on a support for methane coupling via a sequential process. They propose that the catalyst can further contain, inter alia, iron, cobalt or a metal of the actinide or lanthanide series. They opine that Group VIII noble metal, nickel or Group lB noble metal would dissociatively chemisorb methane; Group VIB reducible metal oxides would be reduced by adsorbed hydrogen and thus produce water, and Group IIA metal oxides would convert the adsorbed methane to carbides. The postulated carbides were stated by the patentees to be intermediates in the formation of aromatic compounds. The catalysts are described as being supported on a refractory support such as alumina. The catalyst is disclosed as being operated in a sequential (or pulsed) mode in which the oxygen containing gases and methane containing gases are alternatively cycled to the reaction zone. The catalyst becomes coked with use and therefore requires periodic regeneration.

Garcia, et al., "Direct Catalytic Synthesis of Ethylene from Methane", React. Kinet. Catal. Lett., Vol. 28, 481 (1985), disclose the use of, e.g., platinum and cobalt containing catalysts for oxidative coupling. The authors operated in the sequential mode and noted that long induction Periods are required between detecting higher hydrocarbon products.

"It is interesting to note the long inductive periods required for achieving detectable conversions. ". . . This would indicate that ethylene (sic) production can only occur when a significant surface carbon concentration is reached." (p. 434).

The role of Co is postulated to ". . . chemisorb $CH_4$ dissociatively and provide additional surface species," (p. 435) and play ". . .the role of oxygen donor. . ." (p. 435).

Workers have reported numerous transition metal oxides supported on silica as methane coupling catalysts in sequential processes. See, for instance, U.S. Pat. No. 4,443,644 ($SB_2O_3$); U.S. Pat. No. 4,443,645 ($GeO_2$); U.S. Pat. No. 4,443,646 ($Bi_2O_3$); U.S. Pat. No. 4,443,649 (PbO); U.S. Pat. No. 4,443,648 ($In_2O_3$); U.S. Pat. No. 4,443,649 ($Mn_3O_4$); U.S. Pat. No. 4,444,984 ($SnO_2$); U.S. Pat. No. 4,489,215 (Ru oxide); U.S. Pat. No. 4,593,139 (Ru oxide); and GB No. 2156842 (Mn, Sn, In, Ge, Pb, Sb, and Bi - oxides). In a summary (J. A. Sofranko, et al., J Catal, 103, 302 (1987)), manganese-silica catalysts were reported to give the best $C_2$ (ethylene and ethane) yields. Alkali metal and alkaline earth metal doping, especially sodium, of the manganese-silica catalysts (C. A. Jones, et al., J. Catal., 103, 311 (1987)) is reported to enhance the methane coupling ability. A 15% Mn - 5% $Na_4O_2O_7$ - silica catalyst reportedly gave 17% yields of $C_2$ and higher hydrocarbons for 2 minute runs at 850° C. in a sequential process. The beneficial effect of sodium addition is Postulated by the authors to be due to increased surface basicity, reduction of surface area and a specific manganese-sodium interaction.

Numerous materials have been reported as dopants, supports, promoters and stabilizers for the manganese based methane coupling catalyst. See, for instance, U.S. Pat. No. 4,495,374; U.S. Pat. No. 4,499,322; U.S. Pat. No. 4,544,784; U.S. Pat. No. 4,544,785; U.S. Pat. No. 4,544,786; U.S. 4,547,608; U.S. Pat. No. 4,547,611; U.S. Pat. No. 4,613,718; U.S. Pat. No. 4,629,718; U.S. Pat. No. 4,650,781; U.S. Pat. No. 4,654,459; U.S. 4,670,619; U.S. Pat. No. 4,769,508; U.S. Pat. No. 4,777,313; WO No. 85/00804; and EP No. 253,522.

Other materials reported as methane coupling catalysts in sequential processes include reducible lanthanide oxides. A. M. Gaffney reports that $Pr_6O_{11}$ (U.S. Pat. No. 4,499,323), $CeO_2$ (U.S. Pat. No. 4,499,324); and $Tb_4O_7$ (U.S. Pat. No. 4,727,212) are effective methane coupling catalysts after doping with alkali metal or alkaline earth metal compounds. The sodium-promoted nonstoichiometric oxide, 4% Na on $Pr_6O_{11}$, is reported to be the most active and selective, giving in the sequential mode 21% methane conversion and 76% selectivity to $C_2$ and higher hydrocarbons at 800° C. and 1.4 WHSV (weight hourly space velocity) (See Gaffney, et al., J. Catal., 114, 422 (1988)).

A typical response from sequential mode catalysts is that the selectivity to $C_2$ and higher hydrocarbons increases as the methane coupling catalyst is reduced (methane conversion decreases). Hence, initially when the methane conversion is highest, the selectivity to $C_2$ and higher hydrocarbons is at its minimum. Thus, catalysts are sought in which the selectivity to $C_2$ and higher hydrocarbons is high during the early stages of the catalyst reduction when the rate of conversion is the greatest.

M. Vallet-Regi, et al., (J. Chem. Soc. Dalton Trans., 775 (1988)) have disclosed a double perovskite of the formula $LaCaMnCoO_6$. This material is said to undergo reduction according to the reaction:

$$LaCaMn^{4+}Co^{3+}O_6 + H_2 \rightarrow LaCaMn^{3+}Co^{2+}O_5 + H_2O.$$

SUMMARY OF THE INVENTION

By this invention processes are provided for the oxidative coupling of lower molecular weight alkane to produce heavier molecular weight hydrocarbons in the presence of alkali metal-doped, double perovskite catalyst exhibiting high selectivities to higher hydrocarbon. The catalysts are particularly attractive when used in sequential, or pulsed, processes in that during the initial stages of a sequential run (early stage of catalyst reduction) high selectivities to higher hydrocarbons are obtained. The catalysts used in the processes of this invention comprise a double perovskite represented by the empirical formula $LnAMnTO_6$ wherein Ln is at least one of lanthanum, cerium, neodymium, samarium, praeseodymium, gadolinium and dysprosium; A is one or more alkaline earth metals, e.g., magnesium, calcium, barium and strontium; and T is one or more of iron, cobalt and nickel, and alkali metal component in an amount sufficient to enhance the selectivity to higher hydrocarbons. The alkali metal component comprises at least one of lithium, sodium, potassium, rubidium and cesium, referably lithium and/or sodium. The oxidative coupling is conducted under oxidative coupling conditions in the presence of reactive oxygen-containing material. In the aspect of this invention in which the process is conducted in the sequential mode, the reactive oxygen-containing material comprises the double perovskite which yields oxygen during the reaction and can be regenerated by contact with oxygen.

DETAILED DISCUSSION OF THE INVENTION

In accordance with this invention, lower alkane is converted to higher hydrocarbons. The lower alkane preferably comprises at least one of methane, ethane and propane, and because of its abundance and the desire to convert it to higher hydrocarbons, methane is the most preferred component in the feed. The products of the conversion are higher hydrocarbons, especially alkanes and alkenes. Often, the desired conversion products are alkenes of two to four carbon atoms, especially ethylene and propylene. Because of its widespread use in commodity chemicals, product mixtures exhibiting a high selectivity to ethylene are typically preferred.

The hydrocarbon conversion process may be conducted in a variety of ways. Generally, two classes of processes can be used: (a) preferably, a sequential process in which an oxidizing material is contacted with a catalyst having the capacity to retain oxygen in an available state for later reaction and then an alkane-containing feed is contacted with the catalyst in the reaction zone, and (b) a cofeed, or simultaneous process, in which both the oxidizing material and the alkane-containing feed are provided at the same time to the reaction zone.

In the sequential process, the alkane-containing feed may comprise up to essentially 100 percent of this feed stream, e.g., about 25 to essentially 100 volume percent of this feed stream. This feed stream may contain other components which are not unduly deleterious to the oxidative coupling reaction. Accordingly, unless a quasi-cofeed process is sought, the alkane-containing feed stream has an essential absence of oxidizing material, e.g., less than about 10, more preferably less than about 0.5, volume percent oxidizing material. The alkane-containing feed may also contain essentially inert gases such as helium, nitrogen, argon, steam, and carbon dioxide.

When the process is operated in a cofeed mode, the oxidizing material and alkane may be introduced by one or more separate streams or, most commonly, in a premixed stream. Generally, the mole ratio of alkane to active oxygen atom of the oxidizing material (an active oxygen atom is an oxygen atom that is available for oxidation) is at least about 1:2, say, about 1:2 to 50:1, preferably 1:1 to 20:1. The alkane typically comprises at least about 2 volume percent, e.g., up to about 95, say, 5 to 90, volume percent of the total gases fed to the reaction zone. Frequently, the feed streams are diluted with essentially inert gases such as those discussed above. When diluted, the diluent usually provides between about 5 to 95 volume percent of the feed streams.

The oxidizing material may be any suitable oxygen-bearing material which, under the conditions in the reaction zone, yields an active oxygen atom for the oxidative coupling. While not wishing to be limited to theory, the oxygen atom may be provided as reactive in a gaseous zone and/or may be provided on a catalyst surface in, for instance, reacted, absorbed or adsorbed form. Convenient oxidizing materials for cofeed processes, which can also serve as regenerating materials for providing oxygen to the catalyst surface in sequential processes, are normally gaseous such as molecular oxygen, (e.g., as oxygen, enriched air or air), ozone and gases which yield oxygen such as $N_2O$. Oxidizing or regenerating materials that are liquid or solid at ambient conditions may also be used provided that they can be facilely introduced into the reaction zone. In the sequential process, the regeneration of the catalyst with oxygen may conveniently be conducted under process conditions similar to those used for the hydrocarbon conversion. Often, regeneration is favored at higher partial pressures of oxygen, e.g., preferably at least 0.15 or 0.20 atmospheres to 500 or more atmospheres, in oxygen partial pressure. The regeneration is frequently conducted for periods of at least about 1 minute to 12 or more hours. Usually, temperatures of about 650° to 850° C. are used during the regeneration.

The reaction proceeds at elevated temperatures. Generally, a minimum temperature must be achieved before significant higher hydrocarbon production occurs. If the temperature is too high, an undue amount of the hydrocarbon is consumed in oxidation or degradation reactions. Often, the temperature is in the range of about 500° to 1000° C., e.g., about 600° to 850° C. Most frequently, the temperature is within the range of about 675° to 825° C. The reactants are usually preheated prior to their introduction into the reaction zone; for instance, to within about 200° C, preferably about 100° C. of the temperature in the reaction zone.

The pressure in the reaction zone may vary widely from less than atmospheric to 100 atmospheres absolute or more. The pressure is often in the range of about 1 to 100, say, 1 to 50, atmospheres absolute.

In general, the reactions proceed rapidly and, hence, the reactants may reside in the reaction zone under reaction conditions for a relatively short period of time, e.g., less than about 20 seconds, often less than about 10 seconds. Frequently, the residence time is about 0.001 to 5, say, 0.1 to 3, seconds. The gas hourly space velocity based on the total gases fed to the reaction zone to the volume of the reaction zone is often about 50 to 50,000, preferably, 500 to 15000, reciprocal hours. Since alkane conversion reactions do not require the presence of a catalyst to proceed, the overall volume of the vessel in which the reaction takes place may be substantially larger than that of the reaction zone containing catalyst. Even so, the volume of the reaction zone is frequently calculated as the volume of the vessel filled with catalyst.

A vapor phase halogen component may be provided to the reaction zone during the process. It may be added intermittently or continuously. The halogen component may be provided as a solid, liquid or vapor when added. The halogen component may be halogen, e.g., chlorine, bromine or iodine, or a halogen-containing compound. The halogen-containing compounds (chlorine, bromine and iodine-containing compound) may be inorganic such as hydrogen halide, carbon tetrahalide, etc., or organic such as methylene halide, methyl dihalide, methyl trihalide, ethyl halide, ethyl dihalide, ethyl trihalide, ethyl tetrahalide, vinyl halide, sulfonyl chloride, phosphonyl chloride, etc. Often, the organic halides have from 1 to 3 halogen atoms and 1 to 3 carbon atoms. The amount of halogen component which can be added to the process, can vary; however, the amount added should be sufficient to provide the desired yield of higher hydrocarbon and the sought ethylene to ethane mole ratio. With either too little or too much halogen component addition, the catalyst performance will be adversely effected. Most frequently, if too little or too much halogen component has been added, good performance can be achieved by altering the rate of halogen component addition.

The amount of halogen component to be added for a given catalyst system will depend, inter alia, on the nature of the catalyst. Moreover, the optimum amount may change with the use of the catalyst.

Also, the type of halogen being added will influence the performance of the reaction system. In general, a process using a bromine compound as the halogen will provide a higher ratio of ethylene to ethane than a similar process using chlorine compound as the halogen. Within these guidelines, the amount of continuous vapor phase addition of the halogen component is often within the range of 0.1 to 5000, say, 1 to 1000, parts per million by volume based on the volume of feed to the reaction zone.

The reaction may be conducted in any suitable reactor capable of providing the reaction temperatures. The reaction may be conducted in a single or in a series of sequential and/or parallel reactors. In a sequential process, the use of parallel reactors can enable a relatively constant volume product stream to be achieved by operating one or more reactors in the oxidizing (regeneration) mode and one or more reactors in the hydrocarbon conversion mode at a given time and then cycling each bed through the sequence of steps in the process. In another embodiment, the catalyst may be cycled from a regeneration zone to a hydrocarbon conversion zone. The catalyst bed may be of any suitable type, including, but not limited to, fixed, fluid, riser, falling, ebulating, and moving bed.

The catalyst size and configuration may vary depending upon the reactor type. For fluid, ebulating and riser reactors, the catalyst is typically between about 30 and 300 microns in major dimension. In fixed bed reactors, the catalyst may be in any suitable configuration including spheres, pellets, cylinders, monoliths, etc., and the size and shape may be influenced by pressure drop considerations for the gases passing through the bed. Often, the catalyst is at least about 0.2 centimeter, say, about 0.5 to 2 centimeters, in major dimension. Monolithic catalysts, which may comprise a support having the catalytically-active component thereon or which may be homogeneous, can be sized to fit the reactor volume.

The catalysts used in the process of this invention comprise double perovskites. These double perovskites are believed in the crystalline state to exhibit some ordered domains, while in other regions the cations are distributed at random. The proposed ordered structure has $Mn^{+4}$ and $T^{+3}$ (wherein T is one or more of iron, cobalt and nickel, and preferably comprises cobalt) ions occupying alternating (B) sites in adjoining "$ABO_3$" perovskite structures with $Ln^{3+}$ and $A^{2+}$ (wherein A is one or more alkaline earth metal, preferably calcium) ions occupying alternating corner (A) sites.

One proposed procedure for making the double perovskite such as $LnCaMnCoO_6$ is by dissolving stoichiometric amounts of $La(NO_3)_3$, $Co(NO_3)_2$, $MnCO_3$ and $CaCO_3$ in saturated citric acid solution. A diol such as ethylene glycol is added which increases the solution viscosity due to the formation of ester-type three-dimensional polymers. Evaporation of the solution results in a vitreous intermediate polymer containing all the cation in the desired stoichiometric amounts. The organic resin can be eliminated by heating at about 400° to 600° C., preferably at 450° C., for about 4 to 24 hours in a muffle furnace. The resulting material is then calcined, e.g., in air, at temperatures in excess of about 800° C., preferably in excess of at least about 900° C., say 900° to 950° C., for a time sufficient to prepare the crystalline structure. Often, the calcining is for a period of at least about 12 hours, say, about 24 to 72 hours or more, e.g., about 48 to 64 hours. With temperatures that are too low or with too brief a period of calcining, the perovskite structure will either not be formed or will be incompletely formed. If the temperature is too high, the crystal may be destroyed.

While the foregoing technique has been described for making the double perovskite useful in the processes of this invention, the method by which the perovskite is prepared is not in limitation of the invention and other perovskite syntheses may be used. For instance, a nitrate solution of the La, Ca, Mn and Co components in the approximate desired atomic ratio can be sprayed as a fine mix to obtain dried particles of about 3 to 10 microns wherein each particle contains the sought ratio of components. These particles may be used as is (for in situ perovskite generation during the oxidative coupling reaction) or subjected to calcination.

The catalyst further comprises-alkali metal component in an amount sufficient to enhance selectivity to higher hydrocarbon. In the absence of alkali metal, the conversion to the desired higher hydrocarbon products is reduced. While the presence of, e.g., alkaline earth metal component can enable the double perovskite-containing catalyst to exhibit some selectivity toward higher hydrocarbon product, the presence of alkali metal component can substantially enhance selectivity, especially when the process is operated in the sequential mode.

Often the alkali metal component is in an atomic ratio of alkali metal to manganese in the double perovskite of at least about 0.01:1, say about 0.05 to 10:1, preferably about 0.05:1 to 2:1. The alkali metal component may be provided in any convenient chemical form which enables the selectivity-enhancing effect to be achieved. The exact nature of the chemical species and form which provides the selectivity-enhancing effect is not certain; however, various alkali metal compounds may find utility in the catalysts used in this invention including, but not limited to, alkali metal halides such as fluorides, chlorides, bromides and halides; oxides, peroxides; superoxides; carbonates; nitrates; etc.

The double perovskite may be used in particulate form for the catalyst or may be fabricated into a convenient catalyst configuration, e.g., through the use of binders. The perovskite may also be supported on a support (which may or may not have catalytic activity in oxidative coupling reactions) which is capable of withstanding the oxidative coupling conditions, e.g., alumina, spinel, alkaline earth oxides, and the like. Advantageously, the catalyst has a surface area of at least about 0.1, preferably at least about 0.2, say, 0.3 to 100, square meters per gram. The double perovskite often comprises at least about 25, preferably, about 50 to essentially 99 or more, percent by weight of the catalytically-active components of the catalyst.

The catalysts may contain one or more alkaline earth metal components not incorporated into the perovskite structure. If present, these components are generally in an amount of at least 0.01, say, about 0.1 to 60, and typically, 1 to 30, weight percent based on the total weight of the catalyst. These components include compounds of one or more of beryllium, magnesium, calcium, strontium and barium. These compounds may be in the form of, e.g., oxides, hydroxides, peroxides, superoxides and salts such as halides (chloride, bromide, iodide), carbonates, nitrates, etc.

The catalysts used in the processes of this invention may contain other adjuvants such as Group IIIA (including lanthanide series) components such as lanthanum oxide, Group IVA components (e.g., titania and zirconia), Group VA components, Group VIA components such as manganese. These other adjuvants may be present in amount of about 0.0001 to 10 or more weight percent based on the total weight of the catalyst.

Supported catalysts may be prepared by any convenient technique. Techniques which have been proposed include coating the catalyst support with a slurry or paste of the ingredients or impregnating the support using a solution or suspension or complex of the ingredients (the impregnation may be simultaneous for all components or sequential). The impregnation may be by an incipient wetness technique or by immersion in the mother liquor or by evaporating solvent from a solution or suspension containing the catalyst support. The catalysts may be dried and, optionally, calcined.

The support material may comprise refractory oxides, e.g., alumina, zirconia, titania, silica, spinels, perovskites (e.g., $ABO_3$ wherein A is a group IIA metal and B is a Group IVA metal), aluminosilicates, alkaline earth oxides (e.g., magnesium oxide, calcium oxide, barium oxide and strontium oxide); alkaline earth carbonates (e.g., barium carbonate and strontium carbonate), and the like. Advantageously, the support material has a surface area of at least about 0.1, preferably, at least about 0.2, say 0.2 to 60 or 100 or more, square meters per gram. (Determined by the nitrogen B.E.T. Method, J. Am. Chem. Soc., Vol. 60, 309 (1938).

In conducting the processes of this invention, the catalyst may lose selectivity to the higher hydrocarbon product. In some instances, providing additional alkali metal component to the catalyst after loss in selectivity may at least partially regenerate the catalyst performance. The alkali metal component may be added in any convenient manner, e.g., the catalyst may be reimpregnated with an alkali metal component-containing solution or solid, liquid or vaporous alkali component may be deposited on the catalyst.

The following examples are provided by way of illustration of the invention and are not in limitation thereof. All parts and percentages of solids are by weight and of liquids and gases are by volume unless otherwise noted or clear from the context.

EXAMPLE 1

Catalyst A: ($LaCaMnCoO_6$) Preparation of the double perovskite catalyst is similar to the procedures reported by Maria Vallet-Regi, Ester Garcia, and Jose M. Gonzalez-Calbet (J. Chem. Soc., Dalton Trans., 1988) for double perovskites of the formula $LaCaMnCoO_6$. Approximately 12.98 g of $La(NO_3)_3$ (Aldrich Chemical Company, Milwaukee, Wis., 99.999%), 7.36 g of $CaCO_3$ (Aldrich 99.999%), and 4.60 g of $MnCO_3$ (Aldrich 99.999%) are weighed into a 500 mL beaker containing a stirring bar and 100 mL of a saturated solution of citric acid is added with vigorous stirring. The solution is stirred until it is clear. Then, about 53 to 60 mL ethylene glycol (Aldrich 99+%) is added. The solution is then reduced in volume by evaporation. As the liquid evaporates the solution turns brown in color and becomes thick. As solids form, an additional 50 mL of the saturated citric acid solution are added. After evaporating to approximately ⅔ of the starting volume, the solution is placed in a vacuum oven at 130° C. for about 8 to 15 hours. Then it is transferred to an alumina crucible and heated in a muffle furnace at 200° C. for about 4 to 8 hours, 500° to 600° C. for about 8 to 24 hours, and at 900° to 950° C. for about 48 to 72 hours. Powder x-ray analysis of the resulting product agrees with patterns reported for $LaCaMnCoO_6$. This double perovskite is used in the preparation of catalysts B to F.

Catalyst B: (20 wt. % $Na_2C_3$/ $LaCaMnCoO_6$) One part (about 1 g) by weight $Na_2CO_3$ (Johnson-Matthey Aesar Corp., Seabrook, N.H. 99.999%) and 4 parts (about 4 g) by weight $LaCaMnCoO_6$ are added to 150 mL deionized water. The mixture is evaporated with constant stirring to a thick paste. The resulting paste is then dried in a vacuum oven at 110° to 130° C. The resulting black solid is transferred to alumina crucibles and heated in a muffle furnace at 800° C. for approximately 24 hours.

Catalyst C: (24 wt. % $K_2CO_3$/$LaCaMnCoO_6$) About 3.87 g $K_2CO_3$ (Aesar 99.99%) and 12.00 g $LaCaMnCoO_6$ are added to 150 mL deionized water. This mixture is evaporated to a thick paste with constant stirring. The resulting paste is dried in a vacuum oven at 110° to 130° C. The resulting black solid is transferred to alumina crucibles and heated in a muffle furnace at 800° C. for about 2 to 15 hours.

Catalyst D: (15 wt. % $Li_2CO_3$/$LaCaMnCoO_6$) About 2.59 g $Li_2CO_3$ (Aldrich 99.999%) and 15.00 g $LaCaMnCoO_6$ are added to 100 mL deionized water. This mixture is evaporated to a thick paste with constant stirring. The resulting paste is dried in a vacuum oven at 110° to 130° C. The resulting black solid is transferred to alumina crucibles and heated in a muffle furnace at 800° C. overnight.

Catalyst E: (48 wt. % $Rb_2CO_3$/$LaCaMnCoO_6$) About 7.62 g $Rb_2CO_3$ (Aesar 99.99%) and 8.08 g $LaCaMnCoO_6$ are added to 75 mL deionized water. This mixture is evaporated to a thick paste with constant stirring. The resulting paste is dried in a vacuum oven at about 110° to 130° C. The resulting black solid is transferred to alumina crucibles and heated in a muffle furnace at 700° C. for 4 hours.

Catalyst F: (51 wt. % $Cs_2CO_3$-$LaCaMnCoO_6$) About 8.47 g $Cs_2CO_3$ (Aesar 99.999%) and 8.02 g $LaCaMnCoO_6$ are added to 100 mL deionized water. This mixture is evaporated to a thick paste with constant stirring. The resulting paste is dried in a vacuum oven at about 110° to 130° C. The resulting black solid is transferred to alumina crucibles and heated in a muffle furnace at 600° C. for 4 hours.

Catalyst G: ($Mn(CH_3CO_2)_2$-$Na_4P_2O_7$-silica) About 6.6 g $Mn(CH_3COO)_2.4H_2O$ (Aldrich 99.999%) are dissolved in 18.6 mL water. To this solution 8.5 g silica (Aesar 99.5%, 60-325 mesh, 230 $m^2/g$ surface area) are added. The mixture is stirred to ensure that all particles are wet and then placed in a vacuum oven at 130° C. for 3 hours and a muffle furnace at 500° C. for 16 hours. About 0.60 g $Na_4O_2O_7.10H_2O$ (reagent grade) are dissolved in 18.5 mL deionized water and the previously prepared Mn/silica solids are added. The solids are mixed well to ensure wetness of all particles and placed in a vacuum oven at 130° C. for 1.5 hours. Solids are transferred to an alumina crucible and placed in muffle furnace for 16 hours at 850° C.

Catalyst H: (20 wt. % $Na_2CO_3$/$Pr_6O_{11}$) In a 100 mL beaker. 4.00 g $Na_2CO_3$ (Aesar 99.999%) are added to 50 mL deionized water. Then 16 g $Pr_6O_{11}$ (Aldrich 99.99%) are added to the solution. The solution is evaporated until a thick paste remains. The paste is dried in a vacuum oven at 130° C. for 4 hours. The solids are then transferred to alumina crucibles and heated in a muffle furnace at 800° C. for 2 hours.

EXAMPLES 2-11

The following sequential mode examples are conducted using the equipment described below. A quartz reactor assembly is used which comprises a quartz reactor section which is 1.5 centimeters inside diameter (i.d.), 1.7 centimeters outside diameter (o.d.) and 12 centimeters in length. A piece of 0.5 cm. i.d. quartz tube (0.7 cm. o.d.) that is 14.0 cm. in length is attached at the inlet end of the reactor section and a piece of 0.2 cm. i.d. quartz tube (0.4 cm. o.d.) that is 24.1 cm. in length is attached at the outlet end of the reactor section. Quartz "O"-ring joint assemblies are at the ends of each of the tubes. The reactor has a total length of 56.5 cm. The reactor is encased in a Lindberg TM oven for the mid-31 centimeters of its length.

The catalyst bed is formed in the quartz reactor section by placing quartz wool at the outlet end of the reactor section, forming the bed of catalyst particles, placing quartz wool over the bed and filling the rest of the reactor section with quartz chips (20 to 40 mesh).

Charged reactors are flushed with air while the reactor temperature is raised to the desired value. Then, the catalyst is conditioned with flowing air (100 to 250 cc/min.) for 1 to 2 hours. After conditioning, the air flow is stopped and the reactor is flushed with nitrogen. Nitrogen flow is stopped, methane flow is initiated, and samples of gaseous product are collected immediately after exiting the reactor during timed intervals using gas sampling bags. Sample collection is initiated as soon as the methane flow is started. The reactor is then flushed with nitrogen, the reactor temperature is set to the desired value, the catalyst is reconditioned with air, and the process is repeated. The reactor pressure is between 0 and 2.5 psig (101 to 118 kpa absolute) and the feed is usually 100% methane. Collected samples are analyzed using GC methods that quantitatively determine methane, oxygen, nitrogen, ethane, ethylene, propane, propene, carbon monoxide and carbon dioxide. $C_4$ hydrocarbons are qualitatively detected.

In the sequential run tables of results "$CH_4$ Conv." is the percent of methane reacted based on the molar amount of reactant and the total molar amount of carbon present in the product stream. Carbon balances are not obtained. "$C_2$ Sel." and "$C_3$ Sel." are based on the mole of carbon converted to $C_2$'s or $C_3$'s compared to the total moles of carbon in the observed products. The "$C_2$ Yield" is the ["$CH_4$ Conv." X "$C_2$ Sel."]/100. The ethylene to ethane molar ratio is represented by =/— and $CO_2/CO$ is the molar ratio of carbon dioxide to carbon monoxide. "Collection" gives the time interval since the flow of methane through the reactor was started. It is the time interval in which the gaseous sample is collected. "Temp" is the temperature of the furnace at the location of the reactor section. The gas hourly space velocity, "GHSV", is based on the volumetric flow rate of the feed at ambient temperature and pressure per volume of the reactor occupied by the catalyst. The air flow rate during regeneration is measured in cubic centimeters per minute at ambient laboratory conditions.

EXAMPLE 2 (Control)

Results obtained with the reactor section filled with 20-40 mesh quartz chips using the equipment and procedures described previously are summarized in Table II.

TABLE II

| Temp. (°C.) | Flow (ccm) | Collection (min.) | CH$_4$ Conv. % | C$_2$ Sel. % | C$_3$ Sel. % | C$_2$ Yield % | =/− | CO$_2$/CO |
|---|---|---|---|---|---|---|---|---|
| 800 | 50 | 0–1 | 0.34 | 80.8 | 2.0 | 0.28 | 0.42 | 1.32 |
| 800 | 50 | 1–5 | 0.24 | 83.2 | 1.95 | 0.20 | 0.39 | 0.76 |
| 800 | 50 | 5–15 | 0.09 | 91.5 | 0.89 | 0.09 | 0.18 | 0.53 |
| 850 | 50 | 0–1 | 0.29 | 80.9 | 3.05 | 0.24 | 0.60 | 2.01 |
| 850 | 50 | 1–5 | 0.23 | 81.6 | 3.84 | 0.19 | 0.60 | 0.75 |
| 850 | 50 | 5–15 | 0.20 | 84.8 | 2.96 | 0.17 | 0.53 | 0.45 |
| 906 | 50 | 0–1 | 0.34 | 83.3 | 7.07 | 0.28 | 1.16 | 1.24 |
| 906 | 50 | 1–5 | 0.31 | 82.3 | 7.10 | 0.25 | 1.18 | 0.58 |
| 906 | 50 | 5–15 | 0.22 | 80.7 | 2.64 | 0.18 | 0.54 | 1.18 |
| 950 | 50 | 0–1 | 0.57 | 75.3 | 10.7 | 0.43 | 2.33 | 0.38 |
| 950 | 50 | 1–5 | 0.54 | 73.3 | 9.84 | 0.49 | 2.17 | 0.83 |
| 950 | 50 | 5–15 | 0.64 | 72.2 | 9.97 | 0.46 | 2.12 | 1.26 |

EXAMPLE 3 (Comparison)

Results obtained with 15.0 g of Catalyst A using the equipment and procedures described previously are summarized in Table III.

TABLE III

| Temp. (°C.) | GHSV (Hr$^{-1}$) | Collection (min.) | CH$_4$ Conv. % | C$_2$ Sel. % | C$_3$ Sel. % | C$_2$ Yield % | =/− | CO$_2$/CO |
|---|---|---|---|---|---|---|---|---|
| Pretreatment: 700° C.; Air = 100 ccm; 1 hour | | | | | | | | |
| 700 | 529 | 0–2.5 | 2.18 | 5.86 | 0.0 | 0.13 | 0.45 | ** |
| Regenerated: 800° C.; Air = 100 ccm; 1 hour | | | | | | | | |
| 800 | 529 | 0–2.5 | 15.44 | 0.7 | 0.0 | 0.11 | 0.63 | 172 |
| Regenerated: 850° C.; Air = 100 ccm; 1 hour | | | | | | | | |
| 850 | 529 | 0–2.5 | 5.56 | 0.91 | 10.00 | 0.05 | 0.65 | 33.15 |
| Regenerated: 900° C.; Air = 100 ccm; overnight | | | | | | | | |
| 900 | 529 | 0–2.5 | 10.66 | 0.21 | 0.00 | 0.02 | 0.44 | 0.23 |
| Regenerated: 900° C.; Air = 100 ccm; overnight | | | | | | | | |
| 900 | 529 | 0–2.5 | 11.42 | 0.19 | 0.00 | 0.02 | 0.48 | 0.22 |
| Regenerated: 850° C.; Air = 100 ccm; 1 hour | | | | | | | | |
| 850 | 529 | 0–2.5 | 28.65 | 1.05 | 0.00 | 0.30 | 0.62 | 201 |
| Regenerated: 800° C.; Air = 100 ccm; 1 hour | | | | | | | | |
| 800 | 529 | 0–2.5 | 13.73 | 0.34 | 0.00 | 0.05 | 0.52 | 0.85 |

**No CO observed

EXAMPLE 4

Results obtained with 10.0 g of Catalyst B using the equipment and procedures described previously are summarized in Table IV.

TABLE IV

| Temp. (°C.) | GHSV (Hr$^{-1}$) | Collection (min.) | CH$_4$ Conv. % | C$_2$ Sel. % | C$_3$ Sel. % | C$_2$ Yield % | =/− | CO$_2$/CO |
|---|---|---|---|---|---|---|---|---|
| Pretreatment: 800° C.; Air = 100 ccm; overnight | | | | | | | | |
| 800 | 174 | 0–2 | 10.63 | 88.57 | 2.83 | 9.42 | 1.65 | ** |
| 800 | 174 | 2–5 | 7.61 | 85.47 | 3.19 | 6.50 | 1.63 | ** |
| 800 | 174 | 5–10 | 6.92 | 78.39 | 3.82 | 5.43 | 1.68 | 46.52 |
| Regenerated: 800° C.; Air = 200 ccm; 2 hours | | | | | | | | |
| 800 | 523 | 0–2 | 7.30 | 90.59 | 2.19 | 6.62 | 1.07 | 13.59 |
| 800 | 523 | 2–5 | 5.43 | 85.32 | 0.00 | 4.64 | 0.97 | 19.07 |
| Regenerated: 850° C.; Air = 50 ccm; 3 days | | | | | | | | |
| 850 | 174 | 0–2 | 10.04 | 80.27 | 4.17 | 8.06 | 1.76 | 20.45 |
| 850 | 174 | 2–5 | 6.06 | 60.87 | 2.96 | 3.69 | 1.24 | 21.70 |
| 850 | 174 | 5–10 | 4.23 | 24.99 | 0.95 | 1.06 | 0.65 | 5.59 |
| Regenerated: 825° C.; Air = 50 ccm; overnight | | | | | | | | |
| 825 | 174 | 0–2 | 12.18 | 75.69 | 3.86 | 9.22 | 2.40 | 124 |
| 825 | 174 | 2–5 | 11.47 | 66.08 | 4.68 | 7.58 | 2.49 | 42.61 |
| 825 | 174 | 5–10 | 10.84 | 55.14 | 4.41 | 5.98 | 2.35 | 42.17 |
| Regenerated: 825° C.; Air = 200 ccm; 2 hours | | | | | | | | |
| 825 | 523 | 0–2 | 9.69 | 85.39 | 3.21 | 8.27 | 1.47 | 25.89 |
| 825 | 523 | 2–5 | 6.59 | 76.77 | 3.28 | 6.16 | 1.30 | 37.40 |
| Pretreatment: 800° C.; Air = 100 ccm; overnight | | | | | | | | |
| 800 | 523 | 0–2 | 9.04 | 86.05 | 2.42 | 7.78 | 1.30 | 29.06 |
| 800 | 523 | 2–5 | 8.04 | 80.62 | 2.61 | 6.48 | 1.18 | 39.23 |
| 800 | 523 | 5–10 | 5.22 | 75.18 | 2.17 | 3.93 | 0.90 | 19.69 |
| Regenerated: 800° C.; Air = 200 ccm; 2 hours | | | | | | | | |
| 800 | 174 | 0–2 | 10.61 | 84.24 | 2.72 | 8.94 | 1.92 | ** |
| 800 | 174 | 2–5 | 9.35 | 81.58 | 0.00 | 7.63 | 2.08 | 46.98 |

**No CO observed

EXAMPLE 5

Results obtained with 10.0 g of Catalyst C using the equipment and procedures described previously are summarized in Table V.

TABLE V

| Temp. (°C.) | GHSV (Hr$^{-1}$) | Collection (min.) | CH$_4$ Conv. % | C$_2$ Sel. % | C$_3$ Sel. % | C$_2$ Yield % | =/− | CO$_2$/CO |
|---|---|---|---|---|---|---|---|---|
| Pretreatment: 800° C.: Air = 50 ccm; overnight | | | | | | | | |
| 800 | 222 | 0–2 | 6.81 | 75.48 | 0.40 | 5.14 | 0.61 | ** |
| 800 | 222 | 2–5 | 5.38 | 68.43 | 1.03 | 3.68 | 1.02 | 17.87 |
| 800 | 222 | 5–10 | 3.82 | 45.18 | 1.06 | 1.73 | 0.89 | 17.21 |
| Regenerated: 800° C.; Air = 175 ccm; 5 hours | | | | | | | | |
| 800 | 667 | 0–2 | 4.70 | 83.17 | 0.83 | 3.91 | 0.77 | 10.27 |
| 800 | 667 | 2–5 | 3.24 | 54.07 | 1.02 | 1.75 | 0.63 | 16.12 |
| Regenerated: 850° C.; Air = 50 ccm; overnight | | | | | | | | |
| 850 | 222 | 0–2 | 5.94 | 66.33 | 0.57 | 3.94 | 0.72 | ** |
| 850 | 222 | 2–5 | 4.36 | 62.73 | 1.07 | 2.73 | 0.91 | 16.89 |
| 850 | 222 | 5–10 | 2.39 | 31.78 | 0.67 | 0.76 | 0.97 | 5.43 |
| Regenerated: 850° C.; Air = 200 ccm; 2 hours | | | | | | | | |
| 850 | 667 | 0–2 | 7.26 | 76.94 | 1.06 | 5.58 | 0.96 | 18.27 |
| 850 | 667 | 2–5 | 3.89 | 43.18 | 1.69 | 1.68 | 0.75 | 9.21 |
| 850 | 667 | 5–10 | 18.01* | 1.29 | 0.25 | 0.23 | 0.78 | 0.28 |
| Regenerated: 850° C.; Air = 200 ccm; 2.5 hours | | | | | | | | |
| 850 | 667 | 0–2 | 7.60 | 79.48 | 1.10 | 6.04 | 1.00 | 6.84 |
| 850 | 667 | 2–5 | 3.59 | 42.31 | 0.58 | 1.52 | 0.75 | 9.04 |
| 850 | 667 | 5–10 | 10.95* | 0.37 | 0.00 | 0.04 | 0.76 | 0.06 |
| Regenerated: 825° C.; Air = 200 ccm; overnight | | | | | | | | |
| 825 | 222 | 0–2 | 5.23 | 83.54 | 0.57 | 4.37 | 0.90 | ** |
| 825 | 222 | 2–5 | 3.89 | 83.43 | 1.18 | 3.25 | 0.97 | ** |
| 825 | 222 | 5–10 | 3.40 | 68.38 | 1.89 | 2.32 | 0.85 | 11.41 |
| Regenerated: 825° C.; Air = 200 ccm; 2 hours | | | | | | | | |
| 825 | 667 | 0–2 | 9.39 | 79.64 | 1.19 | 7.48 | 1.26 | 23.10 |
| 825 | 667 | 2–5 | 5.96 | 57.79 | 1.04 | 3.45 | 0.89 | 28.35 |
| 825 | 667 | 5–10 | 3.47 | 24.16 | 0.24 | 0.84 | 0.48 | 19.25 |

*Detectable amounts of hydrogen present in the 5 to 10 min. sample
**No CO observed

EXAMPLE 6

Results obtained with 10.1 g of Catalyst D using the equipment and procedures described previously are summarized in Table VI.

TABLE VI

| Temp. (°C.) | GHSV (Hr$^{-1}$) | Collection (min.) | CH$_4$ Conv. % | C$_2$ Sel. % | C$_3$ Sel. % | C$_2$ Yield % | =/− | CO$_2$/CO |
|---|---|---|---|---|---|---|---|---|
| Pretreatment: 800° C.; Air = 200 ccm; 2 hours | | | | | | | | |
| 800 | 263 | 0–2 | 9.83 | 88.20 | 3.15 | 8.67 | 1.44 | ** |
| 800 | 263 | 2–5 | 5.18 | 92.50 | 2.79 | 4.80 | 0.89 | ** |
| 800 | 263 | 5–10 | 1.89 | 91.60 | 2.25 | 1.73 | 0.56 | ** |
| Regenerated: 800° C.; Air = 200 ccm; 3 hours | | | | | | | | |
| 800 | 789 | 0–2 | 8.49 | 89.29 | 3.65 | 7.58 | 1.01 | 6.03 |
| 800 | 789 | 2–5 | 3.50 | 95.82 | 0.00 | 3.35 | 0.58 | ** |
| 800 | 789 | 5–10 | 1.84 | 93.06 | 1.33 | 1.72 | 0.41 | ** |
| Regenerated: 850° C.; Air = 100 ccm; overnight | | | | | | | | |
| 850 | 263 | 0–2 | 10.11 | 89.72 | 3.74 | 9.08 | 1.36 | 22.30 |
| 850 | 263 | 2–5 | 4.94 | 90.63 | 5.38 | 4.48 | 1.03 | ** |
| 850 | 263 | 5–10 | 3.14 | 89.61 | 4.73 | 2.81 | 0.86 | ** |
| Regenerated: 850° C.; Air = 100 ccm; 4 hours | | | | | | | | |
| 850 | 789 | 0–2 | 7.88 | 91.21 | 4.23 | 7.19 | 1.15 | 3.05 |
| 850 | 789 | 2–5 | 3.84 | 94.47 | 3.68 | 3.63 | 0.78 | ** |
| 850 | 789 | 5–10 | 1.79 | 89.97 | 2.43 | 1.61 | 0.45 | ** |
| Regenerated: 850° C.; Air = 100 ccm, overnight | | | | | | | | |
| 750 | 263 | 0–2 | 7.59 | 88.95 | 5.57 | 6.75 | 1.15 | ** |
| 750 | 263 | 2–5 | 4.59 | 92.25 | 3.96 | 4.24 | 0.79 | ** |
| 750 | 263 | 5–10 | 2.56 | 94.68 | 1.77 | 2.43 | 0.51 | ** |
| Regenerated: 750° C.; Air = 200 ccm; 4.5 hours | | | | | | | | |
| 750 | 789 | 0–2 | 2.75 | 91.00 | 1.49 | 2.50 | 0.36 | ** |
| 750 | 789 | 2–5 | 2.12 | 92.95 | 1.11 | 1.97 | 0.32 | ** |
| Regenerated: 750° C.; Air = 100 ccm; overnight | | | | | | | | |
| 700 | 263 | 0–2 | 5.23 | 70.14 | 1.09 | 3.88 | 0.61 | ** |
| 700 | 263 | 2–5 | 2.80 | 72.45 | 0.82 | 2.03 | 0.39 | ** |
| 700 | 263 | 5–10 | 1.98 | 63.19 | 0.59 | 1.25 | 0.28 | ** |
| Regenerated: 700° C.; Air = 200 ccm; 3 hours | | | | | | | | |
| 700 | 789 | 0–2 | 2.20 | 70.20 | 0.35 | 1.54 | 0.24 | ** |
| 700 | 789 | 2–5 | 1.26 | 46.69 | 0.39 | 0.59 | 0.13 | ** |
| 700 | 789 | 5–10 | 0.55 | 56.77 | 0.00 | 0.31 | 0.24 | ** |
| Regenerated: 700° C.; Air = 100 ccm; overnight | | | | | | | | |
| 725 | 789 | 0–2 | 2.99 | 66.20 | 1.30 | 1.98 | 0.29 | 11.63 |
| 725 | 789 | 2–5 | 2.58 | 50.29 | 0.28 | 1.30 | 0.23 | 26.76 |
| 725 | 789 | 5–10 | 1.21 | 87.12 | 0.00 | 1.05 | 0.41 | ** |
| Regenerated: 725° C.; Air = 200 ccm; 4 hours | | | | | | | | |
| Note: Reactant stream switched from 100% CH$_4$ to 20% CH$_4$/ 80% N$_2$ | | | | | | | | |
| 725 | 263 | 0–2 | 29.98 | 48.17 | 1.88 | 14.44 | 1.69 | 371 |

TABLE VI-continued

| Temp. (°C.) | GHSV (Hr$^{-1}$) | Collection (min.) | CH$_4$ Conv. % | C$_2$ Sel. % | C$_3$ Sel. % | C$_2$ Yield % | =/− | CO$_2$/ CO |
|---|---|---|---|---|---|---|---|---|
| 725 | 263 | 2-5 | 20.41 | 55.15 | 2.01 | 11.26 | 1.36 | *** |
| 725 | 263 | 5-10 | 5.91 | 65.56 | 2.36 | 3.88 | 1.15 | ** |
| Regenerated: 725° C.; Air = 200 ccm; 2 hours | | | | | | | | |
| 725 | 789 | 0-2 | 18.17 | 48.75 | 0.84 | 8.86 | 0.75 | 31.27 |
| 725 | 789 | 2-5 | 12.35 | 50.61 | 0.73 | 6.25 | 0.53 | 361 |
| 725 | 789 | 5-10 | 8.14 | 66.54 | 0.77 | 5.41 | 0.44 | ** |

**No CO observed

EXAMPLE 7

Results obtained with 5.0 g of Catalyst E using the equipment and procedures described previously are summarized in Table VII.

TABLE VII

| Temp. (°C.) | GHSV (Hr$^{-1}$) | Collection (min.) | CH$_4$ Conv. % | C$_2$ Sel. % | C$_3$ Sel. % | C$_2$ Yield % | =/− | CO$_2$/ CO |
|---|---|---|---|---|---|---|---|---|
| Pretreatment: 700° C.; Air = 200 ccm; 2 hours | | | | | | | | |
| 700 | 2000 | 0-1 | 1.72 | 64.61 | 0.09 | 1.11 | 0.14 | ** |
| 700 | 2000 | 1-3 | 1.16 | 62.07 | 0.06 | 0.72 | 0.11 | ** |
| 700 | 2000 | 3-10 | 1.11 | 59.87 | 0.26 | 0.66 | 0.14 | ** |
| Regenerated: 700° C.; Air = 200 ccm; Overnight | | | | | | | | |
| 700 | 2000 | 0-1 | 3.87 | 92.03 | 0.15 | 3.56 | 0.24 | ** |
| 700 | 2000 | 1-3 | 2.27 | 94.31 | 0.13 | 2.14 | 0.19 | ** |
| 700 | 2000 | 3-10 | 1.34 | 90.32 | 0.09 | 1.21 | 0.15 | ** |
| Regenerated: 750° C.; Air = 200 ccm; 4 hours | | | | | | | | |
| 750 | 2000 | 0-1 | 4.20 | 96.18 | 0.16 | 4.04 | 0.27 | ** |
| 750 | 2000 | 1-3 | 2.25 | 96.38 | 0.13 | 2.17 | 0.21 | ** |
| 750 | 2000 | 3-10 | 1.27 | 93.03 | 0.08 | 1.18 | 0.19 | ** |
| Regenerated: 750° C.; Air = 200 ccm; 2 hours | | | | | | | | |
| 750 | 2000 | 0-1 | 3.47 | 92.61 | 0.15 | 3.21 | 0.24 | ** |
| 750 | 2000 | 1-3 | 2.39 | 92.93 | 0.13 | 2.22 | 0.23 | ** |
| 750 | 2000 | 3-10 | 2.31 | 80.50 | 0.23 | 1.86 | 0.19 | ** |
| Regenerated: 800° C.; Air = 200 ccm; Overnight | | | | | | | | |
| 800 | 2000 | 0-1 | 3.49 | 93.55 | 0.86 | 3.27 | 0.36 | ** |
| 800 | 2000 | 1-3 | 1.86 | 93.92 | 0.48 | 1.75 | 0.31 | ** |
| 800 | 2000 | 3-10 | 5.09 | 54.49 | 4.46 | 2.78 | 0.41 | 19.9 |
| Regenerated: 800° C.; Air = 200 ccm; 5 hours | | | | | | | | |
| 800 | 2000 | 0-1 | 2.15 | 91.56 | 0.14 | 1.97 | 0.31 | 0.71 |
| 800 | 2000 | 1-3 | 0.80 | 93.14 | 0.14 | 0.74 | 0.23 | ** |
| 800 | 2000 | 3-10 | 2.80 | 3.59 | 0.00 | 0.10 | 0.27 | 0.15 |

**No CO observed

EXAMPLE 8

Results obtained with 5.0 g of Catalyst F using the equipment and procedures described previously are summarized in Table VIII.

TABLE VIII

| Temp. (°C.) | GHSV (Hr$^{-1}$) | Collection (min.) | CH$_4$ Conv. % | C$_2$ Sel. % | C$_3$ Sel. % | C$_2$ Yield % | =/− | CO$_2$/ CO |
|---|---|---|---|---|---|---|---|---|
| Pretreatment: 600° C.; Air = 200 ccm; 3 hours | | | | | | | | |
| 600 | 1429 | 0-1 | 0.21 | 39.49 | 0.00 | 0.08 | 0.12 | ** |
| 600 | 1429 | 1-3 | 0.31 | 56.94 | 0.00 | 0.17 | 1.26 | ** |
| 600 | 1429 | 3-10 | 0.11 | 46.88 | 0.00 | 0.05 | 0.13 | ** |
| Regenerated: 600° C.; Air = 100 ccm; Over the weekend | | | | | | | | |
| 650 | 1429 | 0-1 | 0.53 | 79.04 | 0.65 | 0.42 | 0.06 | ** |
| 650 | 1429 | 1-3 | 0.00 | *** | *** | *** | *** | *** |
| 650 | 1429 | 3-10 | 0.28 | 58.01 | 0.00 | 0.16 | 0.06 | ** |
| Regenerated: 700° C. Air = 200 ccm; 3 hours | | | | | | | | |
| 700 | 1429 | 0-1 | 1.74 | 81.50 | 0.02 | 1.42 | 0.16 | ** |
| 700 | 1429 | 1-3 | 0.84 | 71.35 | 0.00 | 0.60 | 0.08 | ** |
| 700 | 1429 | 3-10 | 0.52 | 58.93 | 0.00 | 0.31 | 0.08 | ** |
| Regenerated: 700° C.; Air = 100 ccm; Overnight | | | | | | | | |
| 700 | 1429 | 0-1 | 2.05 | 83.26 | 0.00 | 1.70 | 0.12 | ** |
| 700 | 1429 | 1-3 | 0.87 | 78.13 | 0.00 | 0.68 | 0.17 | ** |
| 700 | 1429 | 3-10 | 0.38 | 63.42 | 0.00 | 0.24 | 0.06 | ** |
| Regenerated: 725° C.; Air = 200 ccm; 3.5 hours | | | | | | | | |
| 725 | 1429 | 0-1 | 1.82 | 78.52 | 0.00 | 1.43 | 0.12 | ** |
| 725 | 1429 | 1-3 | 1.06 | 65.99 | 0.00 | 0.70 | 0.17 | ** |
| 725 | 1429 | 3-10 | 0.53 | 47.98 | 0.00 | 0.25 | 0.06 | ** |
| Regenerated: 725° C.; Air = 100 ccm; Overnight | | | | | | | | |
| 725 | 1429 | 0-1 | 1.99 | 82.41 | 0.00 | 1.64 | 0.12 | ** |
| 725 | 1429 | 1-3 | 0.87 | 74.16 | 0.00 | 0.64 | 0.08 | ** |
| 725 | 1429 | 3-10 | 0.65 | 64.43 | 0.00 | 0.42 | 0.21 | ** |
| Regenerated: 750° C.; Air = 200 ccm; 4 hours | | | | | | | | |
| 750 | 1429 | 0-1 | 1.77 | 81.36 | 0.00 | 1.44 | 0.18 | ** |
| 750 | 1429 | 1-3 | 0.74 | 69.57 | 0.00 | 0.52 | 0.10 | ** |
| 750 | 1429 | 3-10 | 0.52 | 62.27 | 0.00 | 0.32 | 0.11 | ** |
| Regenerated: 750° C.; Air = 100 ccm; Overnight | | | | | | | | |

TABLE VIII-continued

| Temp. (°C.) | GHSV (Hr$^{-1}$) | Collection (min.) | CH$_4$ Conv. % | C$_2$ Sel. % | C$_3$ Sel. % | C$_2$ Yield % | =/− | CO$_2$/CO |
|---|---|---|---|---|---|---|---|---|
| 750 | 1429 | 0–1 | 1.28 | 91.19 | 0.44 | 1.17 | 0.12 | ** |
| 750 | 1429 | 1–3 | 0.57 | 82.60 | 0.14 | 0.47 | 0.11 | ** |
| 750 | 1429 | 3–10 | 0.31 | 97.15 | 0.00 | 0.39 | 0.09 | ** |
| Regenerated: 750° C.; Air = 200 ccm; 3 hours | | | | | | | | |
| 800 | 1429 | 0–1 | 2.27 | 84.12 | 0.02 | 1.91 | 0.15 | ** |
| 800 | 1429 | 1–3 | 0.91 | 84.03 | 0.00 | 0.76 | 0.10 | ** |
| 800 | 1429 | 3–10 | 0.77 | 77.41 | 0.00 | 0.60 | 0.20 | ** |

**No CO observed
***No conversion observed

EXAMPLE 9 (Comparative)

Comparison case results obtained with 10.0 g of Catalyst G using the equipment and procedures described previously are summarized in Table IX.

TABLE IX

| Temp. (°C.) | GHSV (Hr$^{-1}$) | Collection (min.) | CH$_4$ Conv. % | C$_2$ Sel. % | C$_3$ Sel. % | C$_2$ Yield % | =/− | CO$_2$/CO |
|---|---|---|---|---|---|---|---|---|
| Pretreatment: 800° C.: Air = 100 ccm; 2 hours | | | | | | | | |
| 800 | 135 | 0–2 | 49.71 | 28.22 | 2.34 | 14.03 | 4.80 | 4.25 |
| 800 | 135 | 2–5 | 22.26 | 42.29 | 4.45 | 9.46 | 3.53 | 5.32 |
| Regenerated: 800° C.; Air = 200 ccm; 1 hour | | | | | | | | |
| 800 | 404 | 0–2 | 41.76 | 31.89 | 2.86 | 13.32 | 4.41 | 4.46 |
| Regenerated: 850° C.; Air = 200 ccm; overnight | | | | | | | | |
| 850 | 135 | 0–2 | 55.36 | 25.21 | 1.80 | 13.96 | 5.53 | 2.76 |
| 850 | 135 | 2–5 | 8.56 | 46.44 | 6.97 | 3.98 | 3.60 | 3.92 |
| 850 | 135 | 5–10 | 2.61 | 64.21 | 18.76 | 1.67 | 2.35 | 0.85 |
| Regenerated: 850° C.; Air = 200 ccm; 3 hours | | | | | | | | |
| 850 | 404 | 0–2 | 26.5 | 44.73 | 4.47 | 11.85 | 3.88 | 3.17 |
| 850 | 404 | 2–5 | 5.48 | 69.53 | 8.24 | 3.81 | 2.26 | 2.35 |
| 850 | 404 | 5–10 | 1.93 | 77.21 | 10.78 | 1.49 | 1.10 | 2.04 |
| Regenerated: 850° C.; Air = 200 ccm; overnight | | | | | | | | |
| 825 | 135 | 0–2 | 44.63 | 27.83 | 2.46 | 12.42 | 4.85 | 5.45 |
| 825 | 135 | 2–5 | 7.27 | 57.71 | 8.93 | 4.19 | 3.18 | 4.21 |
| 825 | 135 | 5–10 | 1.70 | 75.44 | 9.01 | 1.28 | 1.71 | 0.93 |
| Regenerated: 825° C.; Air = 200 ccm; 2 hours | | | | | | | | |
| 825 | 404 | 0–2 | 21.2 | 57.58 | 5.70 | 12.21 | 3.35 | 2.89 |
| 825 | 404 | 2–5 | 8.85 | 72.42 | 6.50 | 6.41 | 2.23 | 3.20 |
| 825 | 404 | 5–10 | 4.10 | 77.88 | 8.01 | 3.19 | 1.39 | 2.05 |
| Regenerated: 850° C.; Air = 200 ccm; overnight | | | | | | | | |
| 850 | 404 | 0–2 | 20.76 | 49.73 | 0.54 | 10.32 | 3.89 | 3.24 |
| 850 | 404 | 2–5 | 7.27 | 57.71 | 8.93 | 4.19 | 3.18 | 4.21 |
| 850 | 404 | 5–10 | 1.65 | 84.29 | 5.84 | 1.39 | 1.16 | 0.83 |
| Regenerated: 850° C.; Air = 200 ccm; overnight | | | | | | | | |
| 825 | 135 | 0–2 | 36.83 | 24.49 | 2.37 | 9.02 | 4.71 | 6.13 |
| 825 | 135 | 2–5 | 5.94 | 59.22 | 8.40 | 3.52 | 3.63 | 2.79 |
| 825 | 135 | 5–10 | 2.70 | 68.54 | 9.85 | 1.85 | 2.99 | 0.95 |
| Regenerated: 850° C.; Air = 200 ccm; 2 hours | | | | | | | | |
| 850 | 404 | 0–2 | 29.93 | 44.78 | 3.23 | 13.40 | 4.34 | 3.49 |
| 850 | 404 | 2–5 | 5.94 | 69.71 | 8.89 | 4.14 | 2.44 | 2.43 |

EXAMPLE 10 (Comparative)

Comparison case results obtained with 10.0 g of Catalyst H using the equipment and procedures described previously are summarized in Table X.

TABLE X

| Temp. (°C.) | GHSV (Hr$^{-1}$) | Collection (min.) | CH$_4$ Conv. % | C$_2$ Sel. % | C$_3$ Sel. % | C$_2$ Yield % | =/− | CO$_2$/CO |
|---|---|---|---|---|---|---|---|---|
| Pretreatment: 800° C.; Air = 100 ccm; overnight | | | | | | | | |
| 800 | 380 | 0–2 | 78.43 | 16.18 | 1.06 | 12.69 | 3.85 | 186.4 |
| 800 | 380 | 2–5 | 16.06 | 52.91 | 3.20 | 8.50 | 1.70 | 65.70 |
| 800 | 380 | 5–10 | 1.54 | 54.36 | 1.72 | 0.83 | 0.70 | 1.75 |
| Regenerated: 800° C.; Air = 200 ccm; 3 hours | | | | | | | | |
| 800 | 1139 | 0–2 | 30.33 | 43.81 | 2.81 | 13.29 | 2.08 | 77.87 |
| 800 | 1139 | 2–5 | 2.09 | 73.85 | 1.42 | 1.54 | 0.46 | 5.13 |
| Regenerated: 850° C.; Air = 100 ccm; overnight | | | | | | | | |
| 850 | 380 | 0–2 | 26.18 | 35.02 | 2.31 | 9.17 | 2.25 | 49.65 |
| 850 | 380 | 2–5 | 2.85 | 53.98 | 4.36 | 1.54 | 0.92 | 2.95 |
| Regenerated: 850° C.; Air = 100 ccm; overnight | | | | | | | | |
| 850 | 1139 | 0–2 | 17.61 | 37.47 | 2.12 | 6.60 | 1.66 | 23.52 |
| 850 | 1139 | 2–5 | 2.96 | 24.28 | 0.61 | 0.72 | 0.62 | 0.40 |
| 850 | 1139 | 5–10 | 4.41 | 10.35 | 0.00 | 0.46 | 0.53 | 0.20 |
| Regenerated: 750° C.; Air = 100 ccm; overnight | | | | | | | | |
| 750 | 380 | 0–2 | 35.82 | 69.11 | 4.88 | 24.76 | 3.30 | 31.94 |
| 750 | 380 | 2–5 | 5.85 | 67.12 | 3.82 | 3.93 | 1.27 | 19.55 |
| Regenerated: 750° C.; Air = 200 ccm; 4 hours | | | | | | | | |
| 750 | 1139 | 0–2 | 19.04 | 79.68 | 5.13 | 15.17 | 1.52 | 45.03 |
| 750 | 1139 | 2–5 | 13.32 | 81.94 | 4.02 | 10.92 | 1.12 | 19.00 |

TABLE X-continued

| Temp. (°C.) | GHSV (Hr$^{-1}$) | Collection (min.) | CH$_4$ Conv. % | C$_2$ Sel. % | C$_3$ Sel. % | C$_2$ Yield % | =/− | CO$_2$/CO |
|---|---|---|---|---|---|---|---|---|
| 750 | 1139 | 5–10 | 2.49 | 81.83 | 1.07 | 2.03 | 0.58 | ** |

**No CO observed

EXAMPLE 11

Results obtained with 5.0 g of Catalyst B using the equipment and procedures described previously are summarized in Table XI. Samples are collected for GC/MS analyses to determine the amounts of heavier hydrocarbons formed. Relative amounts based on an assigned value of 100 for ethane are given in Table XII.

TABLE XI

| Temp. (°C.) | GHSV (Hr$^{-1}$) | Collection (min.) | CH$_4$ Conv. % | C$_2$ Sel. % | C$_3$ Sel. % | C$_2$ Yield % | =/− | CO$_2$/CO |
|---|---|---|---|---|---|---|---|---|
| Pretreatment: 800° C.; Air = 200 ccm; 3 hours | | | | | | | | |
| 803 | 1385 | 0–1 | 8.44 | 90.52 | 1.24 | 7.64 | 0.78 | ** |
| 803 | 1385 | 1–3 | 3.70 | 88.98 | 0.94 | 3.29 | 0.47 | ** |
| 803 | 1385 | 3–10 | 1.31 | 86.51 | 0.58 | 1.13 | 0.28 | ** |
| Regenerated: 800° C.; Air = 200 ccm; Overnight | | | | | | | | |
| Samples collected for GC/MS analyses. | | | | | | | | |
| Regenerated; 800° C.; Air = 200 ccm; 2 hours | | | | | | | | |
| 803 | 1385 | 0–1 | 3.98 | 92.98 | 0.63 | 3.70 | 0.35 | ** |
| 803 | 1385 | 1–3 | 2.63 | 94.44 | 0.51 | 2.48 | 0.29 | ** |
| 803 | 1385 | 3–10 | 1.35 | 91.03 | 0.32 | 1.23 | 0.24 | ** |

**No CO observed

TABLE XII

| | Relative Amounts of Gaseous Products Based on Assigned Value of 100 for Ethane | | | | | | | | |
|---|---|---|---|---|---|---|---|---|---|
| Interval | Ethane | Ethylene | Propane | Propylene | Butadiene | Butene | Pentene | C$_5$-Olefins | Benzene |
| 0–1 | 100 | 24 | 3.2 | 1.9 | 4.5 | 0.60 | 0.25 | 0.23 | 0.29 |
| 1–3 | 100 | 24 | 2.6 | 1.3 | 1.7 | ** | ** | ** | ** |
| 3–10 | 100 | 20 | 1.6 | 1.0 | 1.1 | ** | ** | ** | ** |

**Levels too low for detection.

EXAMPLE 12

Fresh, reduced (with methane), and reoxidized after reduction with methane samples of Catalyst B are analyzed by x-ray powder diffraction. For all of the materials, the main crystalline pattern observed is consistent with that reported for LaCaMnCoO$_6$.

EXAMPLE 13

The following example is conducted in the cofeed mode with the equipment described below. A quartz reactor is used which comprises a 1.5 centimeter (inside diameter) quartz tube about 55.9 centimeters in length with quartz "O"-ring joints at each end. At the bottom, a quartz effluent tube extends radially outward. Axially within the reactor tube is another quartz tube (1.3 centimeters outside diameter (1.1 centimeters inside diameter)) extending from the bottom (effluent end) of the reactor for about 28 centimeters. This tube is terminated with a joined 5 centimeters tube axially positioned thereon having an outside diameter of 0.5 centimeter and inside diameter of 0.3 centimeter. The annular region around this thinner tube ("annular reactor portion") receives the catalyst. These inner tubes form a thermocouple well. The thermocouple well extends 33 centimeters into the reactor from the bottom of the tube. The reactor is encased in a Lindberg oven for the mid-31 centimeters of its length. The incoming and exiting lines from the reactor are capable of being sampled by gas chromatography.

The catalyst bed is formed in the reactor by providing 20 to 40 mesh (U.S. Sieve Series) quartz chips around the larger diameter section of the thermocouple well, placing quartz wool over the chips (1 centimeter), forming the bed of catalysts (either 1 or 4 grams) wherein the catalyst particles have an average size of about 100 microns and then placing glass wool over the catalyst (1 centimeter) and either more quartz chips on the glass wool or a combination of an axially extending 1.3 centimeters outside diameter quartz solid rod with the quartz chips in the annular zone around the solid rod, to fill the upper portion of the reactor tube.

In the general operating procedure, the reactor is flushed with nitrogen while heating to about 450° to 500° C. When at that temperature, the catalyst is preconditioned with air flowing at 100 cubic centimeters (at ambient room temperature and pressure) per minute for one hour. After the preconditioning, the reactant stream is fed and the reactor is brought to the desired temperature. periodic analyses of the gases are conducted (usually at intervals between one and two hours). The reactor pressure is about 5 pounds per square inch gauge (135 kpa absolute) and the feed contains CH$_4$/O$_2$/N$_2$ in a mole ratio of about 2/1/3.8.

The results are provided in Table XIII. The abbreviations have the same meanings as set forth for Examples 2 to 11.

The performance of catalyst B in the cofeed mode of operation using the equipment and procedures described previously is summarized in Table XIII. Reactant feed gas ratio of CH$_4$/O$_2$/N$_2$ is 2.0/1/3.8.

TABLE XIII

| Temp. °C. | CH$_4$Conv. % | C$_2$ Sel. % | C$_3$ Sel. % | C$_2$ Yield % | =/— Ratio molar | Time Hr. | GHSV Hr$^{-1}$ |
|---|---|---|---|---|---|---|---|
| 800 | 32.44 | 37.49 | 2.17 | 12.22 | 1.76 | 1 | 3673 |
| 800 | 32.35 | 38.60 | 2.33 | 12.55 | 1.85 | 3 | 3673 |
| 800 | 32.46 | 38.55 | 2.35 | 12.63 | 1.92 | 6 | 3673 |
| 800 | 30.11 | 34.69 | 1.73 | 10.55 | 1.43 | 24 | 3673 |
| 800 | 28.90 | 34.57 | 1.68 | 10.20 | 1.42 | 30 | 3673 |
| 800 | 28.42 | 39.58 | 1.90 | 10.93 | 1.39 | 39 | 3673 |
| 800 | 28.45 | 37.81 | 1.87 | 10.48 | 1.36 | 48 | 3673 |
| 800 | 28.28 | 43.60 | 2.17 | 11.66 | 1.36 | 57 | 3673 |
| 800 | 28.72 | 38.61 | 1.93 | 10.77 | 1.38 | 66 | 3673 |
| 701 | 24.02 | 20.80 | 0.77 | 4.98 | 0.70 | 78 | 1837 |
| 701 | 22.80 | 18.33 | 0.53 | 4.01 | 0.54 | 84 | 1837 |
| 701 | 22.40 | 15.08 | 0.43 | 3.27 | 0.50 | 90 | 1837 |
| 750 | 26.56 | 34.16 | 1.45 | 8.74 | 0.90 | 93 | 3673 |
| 750 | 25.11 | 28.79 | 0.99 | 6.97 | 0.77 | 99 | 3673 |
| 750 | 24.04 | 20.01 | 0.56 | 4.89 | 0.69 | 102 | 3673 |
| 750 | 23.79 | 20.08 | 0.57 | 4.68 | 0.63 | 108 | 3673 |
| 750 | 23.44 | 21.59 | 0.60 | 4.87 | 0.62 | 111 | 3673 |
| 700 | 23.58 | 38.10 | 0.19 | 8.11 | 1.82 | 119 | 3673 |
| 700 | 22.73 | 36.28 | 2.51 | 7.34 | 1.45 | 122 | 3673 |
| 700 | 25.38 | 24.86 | 0.26 | 5.27 | 0.66 | 127 | 3673 |
| 700 | 23.74 | 8.76 | 0.12 | 2.02 | 0.46 | 133 | 3673 |

It is claimed:

1. A catalyst suitable for oxidative coupling of alkanes comprising a catalytically-active amount of double perovskite of the empirical formula LnAMnTO$_6$ wherein A is one or more alkaline earth elements; Ln is one or more of lanthanum, cerium, neodymium, samarium, praseodymium, gadolinium and dysprosium and T is one or more of iron, cobalt and nickel, and alkali metal component in an amount sufficient to enhance selectivity to higher hydrocarbons.

2. The catalyst of claim 1 wherein the alkali metal component comprises at least one of sodium and lithium compound.

3. The catalyst of claim 2 wherein T comprises cobalt.

4. The catalyst of claim 3 wherein Ln comprises lanthanum.

5. The catalyst of claim 4 wherein the atomic ratio of alkali metal to manganese in the double perovskite is about 0.05:1 to 10:1.

* * * * *